United States Patent
Hiraga et al.

(10) Patent No.: US 10,087,139 B2
(45) Date of Patent: Oct. 2, 2018

(54) 3-PHENYLISOSERINE DERIVATIVE PRODUCTION METHOD

(71) Applicant: Toray Fine CHhemicals Co., Ltd., Tokyo (JP)

(72) Inventors: Hisafumi Hiraga, Tokai (JP); Takeshi Nishikawa, Tokai (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 15/554,743

(22) PCT Filed: Feb. 23, 2016

(86) PCT No.: PCT/JP2016/055223
§ 371 (c)(1),
(2) Date: Aug. 31, 2017

(87) PCT Pub. No.: WO2016/140104
PCT Pub. Date: Sep. 9, 2016

(65) Prior Publication Data
US 2018/0237384 A1   Aug. 23, 2018

(30) Foreign Application Priority Data

Mar. 3, 2015 (JP) ................................ 2015-041151

(51) Int. Cl.
| | | |
|---|---|---|
| *C07C 269/00* | (2006.01) | |
| *C07C 231/10* | (2006.01) | |
| *C07C 269/04* | (2006.01) | |
| *C07C 269/06* | (2006.01) | |
| *C07C 231/12* | (2006.01) | |
| *C07C 231/02* | (2006.01) | |

(52) U.S. Cl.
CPC .......... *C07C 269/00* (2013.01); *C07C 231/02* (2013.01); *C07C 231/10* (2013.01); *C07C 231/12* (2013.01); *C07C 269/04* (2013.01); *C07C 269/06* (2013.01)

(58) Field of Classification Search
None
See application file for complete search history.

(56) References Cited

U.S. PATENT DOCUMENTS 5,932,758 A   8/1999 Stingl et al.

FOREIGN PATENT DOCUMENTS

| WO | 93/10076 A1 | 5/1993 |
|---|---|---|
| WO | 97/02236 A1 | 1/1997 |
| WO | 97/07110 A1 | 2/1997 |
| WO | 97/34866 A1 | 9/1997 |
| WO | 03/002509 A1 | 1/2003 |
| WO | 2012/117417 A1 | 9/2012 |

OTHER PUBLICATIONS

Hayashi ("A Novel Approach of Water-Soluble Paclitaxel Prodrug with No Auxiliary and No Byproduct: Design and Synthesis of Isotaxel" J. Med. Chem. 2003, 46, Supporting Information, p. S1-S15). (Year: 2003).*

Deng, L., el al., "A Practical, Highly Enantioselective Synthesis of the Taxol Side Chain via Asymmetric Catalysis," *Journal of Organic Chemistry*, 1992, vol. 57, pp. 4320-4323.

(Continued)

*Primary Examiner* — Jafar F Parsa
*Assistant Examiner* — Amy C Bonaparte
(74) *Attorney, Agent, or Firm* — DLA Piper LLP (US)

(57) ABSTRACT

A method produces a 3-phenylisoserine derivative by protecting an amino group of a compound represented by General Formula (1) (wherein $R^1$ represents a phenyl group, or a phenyl group having a substituent; $R^2$ represents an alkali metal, alkaline earth metal, or nitrogen base; and $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group) in water or a mixed solvent containing water to obtain a particular compound; extracting with a $C_4$ ether-based solvent; replacing at least part of the $C_4$ ether-based solvent with a $C_1$-$C_4$ aliphatic alcohol while removing the $C_4$ ether-based solvent and water to perform esterification reaction; and isolating at 0 to 30° C. to obtain a 3-phenylisoserine derivative represented by General Formula (2).

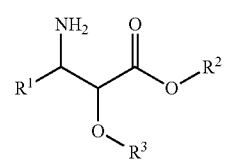

(1)

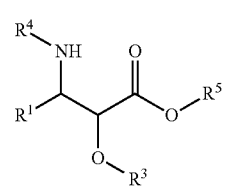

(2)

7 Claims, No Drawings

(56) References Cited

OTHER PUBLICATIONS

Hayashi Y., et al., "A Novel Approach of Water-Soluble Paclitaxel Prodrug with No Auxiliary and No Byproduct: Design and Synthesis of Isotaxel," *Journal of Medicinal Chemistry*, 2003, vol. 46, pp. 3782-3784.
Denis, J., et al., "An Efficient, Enantioselective Synthesis of the Taxol Side Chain," *Journal of Organic Chemistry*, 1986, vol. 51, pp. 46-50.
Kandula, S., et al., "An asymmetric aminohydroxylation route to (+)-L-733,060," *Tetrahedron: Asymmetry*, 2005, vol. 16, pp. 3579-3583.
Shen, X., et al., "An Efficient Semi-Synthetic Method to Construct Docetaxel via Sterically Crowded Linear Side Chain Esterification", *Chin. J. Chem.*, 2013, 31, pp. 31-36, Scheme 2.

\* cited by examiner

3-PHENYLISOSERINE DERIVATIVE PRODUCTION METHOD

TECHNICAL FIELD

This disclosure relates to a method of producing a 3-phenylisoserine derivative, which is important as, for example, an intermediate material for pharmaceuticals.

BACKGROUND

Compounds having a β-amino acid site such as 3-phenylisoserine derivatives are known to be compounds that are industrially useful for pharmaceuticals and the like. Known examples of methods of producing a 3-phenylisoserine derivative include the following:

(1) a method in which methyl phenylglycidate is subjected to a ring-opening reaction with hydrogen azide in the presence of boron trifluoride, and the resulting azide is subjected to benzoylation and catalytic hydrogenation to produce N-benzoyl-3-phenylisoserine methyl ester (see WO 1993/010076);

(2) a method in which 3-phenylisoserine is esterified in methanol, and benzoyl chloride is reacted with its concentrate in water to produce N-benzoyl-3-phenylisoserine methyl ester (see WO 1997/002236); and (3) a method in which 3-phenylisoserine is reacted with benzoyl chloride in water, and the pH of the reaction liquid is changed to an acidic pH to allow precipitation of a crystalline product, followed by isolation of the product by solid-liquid separation to obtain N-benzoyl-3-phenylisoserine (see The Journal of Organic Chemistry (1992), 57(15) 4320-4323).

However, in method (1), use of a highly toxic material and a highly explosive azide intermediate is required, which is industrially problematic.

Method (2) is a production method in which esterification is followed by protection of an amino group. In method (2), 3-phenylisoserine methyl ester is obtained as an intermediate by carrying out the esterification in advance. However, since the intermediate has a free amino group and an ester moiety in the molecule, by-production of an intermolecular or intramolecular amide body may occur during the subsequent reaction for protection of the amino group. Moreover, in general, methyl ester bodies easily cause hydrolysis at the same time, resulting in poor quality and a low yield.

In method (3), N-benzoyl-3-phenylisoserine ester can be obtained by esterification of the crystals isolated by the solid-liquid separation. Since crystals precipitated by acid precipitation are generally very fine, the method has problems from the viewpoint of industrial production such as a requirement of a very long time for the solid-liquid separation and a high liquid-containing rate of the crystals.

It could therefore be helpful to provide an industrially suitable method of producing a 3-phenylisoserine derivative, which is important as a material for pharmaceuticals and the like.

SUMMARY

We thus provide a method of producing a 3-phenylisoserine derivative, comprising: protecting an amino group of a compound represented by General Formula (1):

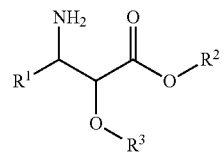

wherein $R^1$ represents a phenyl group, or a phenyl group having a substituent; $R^2$ represents an alkali metal, alkaline earth metal, or nitrogen base; and $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group in water or a mixed solvent containing water to obtain a compound represented by General Formula (2):

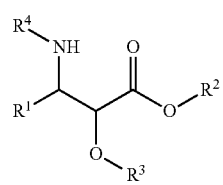

wherein $R^1$ represents a phenyl group, or a phenyl group having a substituent; $R^2$ represents an alkali metal, alkaline earth metal, or nitrogen base; $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group; and $R^4$ represents a formyl group, acetyl group, benzoyl group, tert-butoxycarbonyl group, or benzyloxycarbonyl group;

extracting with a $C_4$ ether-based solvent;

replacing at least part of the $C_4$ ether-based solvent with a $C_1$-$C_4$ aliphatic alcohol while removing the $C_4$ ether-based solvent and water to perform esterification reaction; and isolating at 0 to 30° C. to obtain a 3-phenylisoserine derivative represented by General Formula (3):

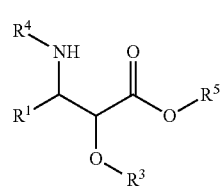

wherein $R^1$ represents a phenyl group, or a phenyl group having a substituent; $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group; $R^4$ represents a formyl group, acetyl group, benzoyl group, tert-butoxycarbonyl group, or benzyloxycarbonyl group; and $R^5$ represents a $C_1$-$C_4$ alkyl group.

When a 3-phenylisoserine derivative is used as a material for a pharmaceutical, the derivative is strongly required to have a purity of not less than 99%. Our method enables production of a 3-phenylisoserine derivative having a purity of not less than 99% by an industrially suitable method.

In our method of producing a 3-phenylisoserine derivative, a 3-phenylisoserine derivative is precipitated as crystals. By taking advantage of low solubility of the desired product in a $C_1$-$C_4$ aliphatic alcohol, the product can be obtained at a purity of not less than 99% by separation from the mother liquor by a solid-liquid separation operation such as filtration or centrifugation followed by a drying step.

DETAILED DESCRIPTION

Our method is described below in detail.

In our method, a compound represented by General Formula (1):

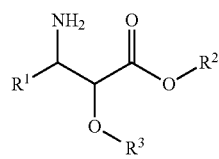

(1)

wherein $R^1$ represents a phenyl group, or a phenyl group having a substituent; $R^2$ represents an alkali metal, alkaline earth metal, or nitrogen base; and $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, acyl protective group of a benzoyl group, trimethylsilyl group, triethylsilyl group, or tert-butyldimethylsilyl group is used as a starting material, and a reaction to protect an amino group is carried out in advance in water or a mixed solvent containing water.

When the esterification reaction described later is carried out in advance, the resulting ester body has a free amino group and an ester moiety in the molecule. Therefore, by-production of an intermolecular or intramolecular amide body occurs during the subsequent reaction for protection of the amino group, and hydrolysis reaction occurs at the same time. This leads to a low quality and a low yield.

In our method, water or a mixed solvent containing water is used. For the mixed solvent containing water, various solvents may be used as the component other than water. Examples of the solvents include ether solvents such as tetrahydrofuran, nitrile solvents such as acetonitrile, and ketone solvents such as acetone, methyl ethyl ketone, and methyl isobutyl ketone. The water or the mixed solvent containing water is preferably water or tetrahydrofuran containing water.

In the compound represented by Formula (1) as a starting material (which may be hereinafter referred to as Compound (1)),

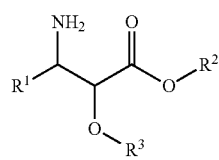

(1)

$R^1$ represents a phenyl group, or a phenyl group having a substituent. Examples of the substituent in the phenyl group having a substituent include $C_1$-$C_4$ alkyl groups, $C_1$-$C_4$ alkoxy groups, and halogen atoms. $R^1$ is preferably a phenyl group, 4-methylphenyl group, 4-methoxyphenyl group, or 4-chlorophenyl group, more preferably a phenyl group.

In Compound (1), $R^2$ represents an alkali metal, alkaline earth metal, or nitrogen base. Examples of the alkali metal include lithium, sodium, and potassium. Examples of the alkaline earth metal include magnesium, calcium, and barium. Examples of the nitrogen base include primary amines such as ammonia, methylamine, benzylamine, and cyclohexylamine; secondary amines such as dimethylamine, dibenzylamine, and dicyclohexylamine; and tertiary amines such as triethylamine and tributylamine $R^2$ is preferably an alkali metal, more preferably lithium, sodium, or potassium, still more preferably sodium or potassium.

In Compound (1), $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group. $R^3$ is preferably a hydrogen atom, benzyl group, methoxymethyl group, benzoyl group, or triethylsilyl group, more preferably a hydrogen atom.

Since Compound (1) has two asymmetric carbons, there are four kinds of optical isomers. Compound (1) may be any single optical isomer, or any mixture of those optical isomers.

Besides Compound (1), Compound (4):

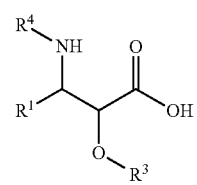

(4)

wherein $R^1$ represents a phenyl group, or a phenyl group having a substituent; $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, acyl protective group of a benzoyl group, trimethylsilyl group, triethylsilyl group, or tert-butyldimethylsilyl group or an inorganic acid salt of Compound (4) may be used as a starting material. When an inorganic acid salt of Compound (4) is used, examples of the inorganic acid include hydrochloric acid, sulfuric acid, nitric acid, phosphoric acid, boric acid, and hydrofluoric acid. The inorganic acid is preferably hydrochloric acid.

Preferably, Compound (1), Compound (4), or an inorganic acid salt of Compound (4) is added after feeding of the water or the mixed solvent containing water.

When Compound (4) or an inorganic acid salt of Compound (4) is used, it is preferred to add a base depending on the valency of the acid to allow the reaction for protection of the amino group to proceed advantageously. Examples of the base include sodium hydroxide, potassium hydroxide, sodium carbonate, sodium hydrogen carbonate, trimethylamine, and pyridine. The base is preferably sodium hydroxide.

Preferably, Compound (1), Compound (4), or an inorganic acid salt of Compound (4) is added after feeding of the water or the mixed solvent containing water, and then an amino-group protecting agent is further added.

The amount of the amino-group protecting agent to be used is preferably 0.8 to 1.2 moles, more preferably 1.0 to 1.1 moles with respect to 1 mole of the Compound (1), Compound (4), or inorganic acid salt of Compound (4).

Examples of the amino-group protecting agent used in our method include formic acid, acetyl chloride, benzoyl chloride, di-tert-butyl dicarbonate, and benzyl chloroformate. The amino-group protecting agent is preferably benzoyl chloride, or di-tert-butyl dicarbonate.

When acetyl chloride, benzoyl chloride, benzyl chloroformate, or the like is used as the amino-group protecting agent, generation of an equimolar of hydrogen chloride occurs as the reaction proceeds. Therefore, the hydrogen chloride is preferably removed by addition of a base. Examples of the base include sodium hydroxide, potassium hydroxide, sodium carbonate, sodium hydrogen carbonate, trimethylamine, and pyridine. The base is preferably sodium hydroxide. The amount of the base to be used is preferably 0.8 to 1.2 moles, more preferably 1.0 to 1.1 moles with respect to 1 mole of the amino-group protecting agent. Preferably, the base is added at the same time as the amino-group protecting agent, or the base and the amino-group protecting agent are alternately added. The pH of the reaction liquid in this process is preferably 7 to 14, more preferably 8 to 13, most preferably 9 to 12.

The temperature during the reaction for protection of the amino group is preferably 0 to 40° C., more preferably 10 to 30° C. The aging time after the addition of the amino-group protecting agent is preferably 30 minutes to 24 hours, more preferably 1 to 12 hours.

A reaction liquid containing a compound represented by General Formula (2):

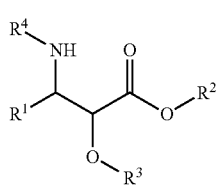

(2)

wherein $R^1$ represents a phenyl group, or a phenyl group having a substituent; $R^2$ represents an alkali metal, alkaline earth metal, or nitrogen base; $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group; and $R^4$ represents a formyl group, acetyl group, benzoyl group, tert-butoxycarbonyl group, or benzyloxycarbonyl group (which may be hereinafter referred to as Compound (2)) is obtained in the manner described above.

In Compound (2), $R^1$ represents a phenyl group, or a phenyl group having a substituent. Examples of the substituent in the phenyl group having a substituent include $C_1$-$C_4$ alkyl groups, $C_1$-$C_4$ alkoxy groups, and halogen atoms. $R^1$ is preferably a phenyl group, 4-methylphenyl group, 4-methoxyphenyl group, or 4-chlorophenyl group, more preferably a phenyl group.

In Compound (2), $R^2$ represents an alkali metal, alkaline earth metal, or nitrogen base. Examples of the alkali metal include lithium, sodium, and potassium. Examples of the alkaline earth metal include magnesium, calcium, and barium. Examples of the nitrogen base include primary amines such as ammonia, methylamine, benzylamine, and cyclohexylamine; secondary amines such as dimethylamine, dibenzylamine, and dicyclohexylamine; and tertiary amines such as triethylamine and tributylamine. $R^2$ is preferably an alkali metal, more preferably lithium, sodium, or potassium, still more preferably sodium or potassium.

In Compound (2), $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group. $R^3$ is preferably a hydrogen atom, benzyl group, methoxymethyl group, benzoyl group, or triethylsilyl group, more preferably a hydrogen atom.

In Compound (2), $R^4$ represents a formyl group, acetyl group, benzoyl group, tert-butoxycarbonyl group, or benzyloxycarbonyl group. $R^4$ is preferably a benzoyl group or a tert-butoxycarbonyl group.

The esterification reaction is preferably carried out through an extraction step and a water removal step that are carried out subsequently without isolation of Compound (2) as an intermediate.

First, the extraction step is described below. In the extraction step, Compound (2) is extracted into a $C_4$ ether-based solvent. Examples of the $C_4$ ether-based solvent include tetrahydrofuran, 1,2-dimethoxyethane, diethylether, and 1,4-dioxane. The $C_4$ ether-based solvent is preferably tetrahydrofuran or 1,2-dimethoxyethane.

The amount of the $C_4$ ether-based solvent to be used is preferably 3 to 10 parts by weight, more preferably 3 to 5 parts by weight with respect to 1 part by weight of the Compound (1), Compound (4), or inorganic acid salt of Compound (4). When a $C_4$ ether-based solvent is used as the mixed solvent containing water in the reaction for protection of the amino group of Compound (1), the amount of the solvent used may be taken into account.

When the $C_4$ ether-based solvent is added, a hydrophobic solvent may be added to increase the liquid separation performance for the water or the mixed solvent containing water. Examples of the hydrophobic solvent include toluene, xylene, chloroform, and dichloromethane. The hydrophobic solvent is preferably toluene.

The amount of the hydrophobic solvent to be used is preferably 0.5 to 3 parts by weight, more preferably 1 to 2 parts by weight with respect to 1 part by weight of the Compound (1), Compound (4), or inorganic acid salt of Compound (4).

After addition of the extraction solvent, an inorganic acid is preferably added. Examples of the inorganic acid include hydrochloric acid, sulfuric acid, nitric acid, phosphoric acid, boric acid, and hydrofluoric acid. The inorganic acid is preferably hydrochloric acid. The amount of the inorganic acid to be added is an amount at which the pH of the reaction liquid becomes preferably 1 to 6, more preferably 2 to 5. When the inorganic acid is added after the addition of the $C_4$ ether-based solvent, precipitation of Compound (2) does not occur so that production of a highly concentrated slurry can be avoided, and an increase in the stirring load can therefore be avoided.

For removal of an inorganic salt derived from the water contained in the thus extracted organic layer, extraction washing may be carried out by addition of water. In this process, a $C_4$ ether-based solvent and/or a hydrophobic solvent may be added to increase the liquid separation performance. The $C_4$ ether-based solvent and the hydrophobic solvent are preferably the same as the solvents used in the extraction step.

The water removal step is described below. In this step, water is removed to allow the esterification reaction, which is carried out subsequently, to proceed advantageously. The water is preferably the contained water that is contained in the extracted organic layer. When a hydrophobic solvent is added, the water layer alone can be selectively removed, for example, using a concentration can equipped with a Dean-Stark apparatus by utilization of the fact that the distillate is separated into two layers, that is, an organic layer and an aqueous layer. The residual water ratio is preferably not more than 2%, more preferably not more than 1% with respect to the entire liquid.

To increase the crystallization yield of the product after the esterification reaction, the $C_4$ ether-based solvent is removed. Since production of a highly concentrated slurry in the can, which causes an increase in the stirring load, cannot be avoided by distillation of the $C_4$ ether-based solvent alone, the $C_1$-$C_4$ aliphatic alcohol used in the esterification reaction is added. The esterification reaction is carried out while replacing at least part of the $C_4$ ether-based solvent with a $C_1$-$C_4$ aliphatic alcohol.

By removing the $C_4$ ether-based solvent by distillation while adding the $C_1$-$C_4$ aliphatic alcohol, concentration can be achieved without causing the production of a highly concentrated slurry in the can, which causes an increase in the stirring load.

The $C_1$-$C_4$ aliphatic alcohol is preferably methanol, ethanol, 1-propanol, 2-propanol, 1-butanol, 2-butanol, isobutanol, or tert-butanol, more preferably methanol or ethanol.

At least part of the $C_4$ ether-based solvent is replaced with a $C_1$-$C_4$ aliphatic alcohol. The residual ratio of the $C_4$ ether-based solvent after the concentration is preferably not more than 20%, more preferably not more than 10% with respect to the entire concentrate.

By using the thus obtained concentrate in the esterification reaction subsequently carried out, the esterification reaction can be carried out directly without isolation of an intermediate as crystals.

The ratio of the $C_1$-$C_4$ aliphatic alcohol in the solvent to perform the esterification reaction is preferably not less than 60%, more preferably not less than 70%.

The esterification reaction is preferably carried out by adding an acid chloride to the concentrate.

A 3-phenylisoserine derivative represented by General Formula (3):

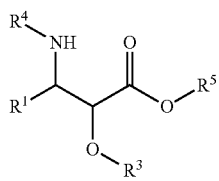

(3)

wherein $R^1$ represents a phenyl group, or a phenyl group having a substituent; $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group; $R^4$ represents a formyl group, acetyl group, benzoyl group, tert-butoxycarbonyl group, or benzyloxycarbonyl group; and $R^5$ represents a $C_1$-$C_4$ alkyl group is obtained by the esterification reaction.

In Compound (3), $R^1$ represents a phenyl group, or a phenyl group having a substituent. Examples of the substituent in the phenyl group having a substituent include $C_1$-$C_4$ alkyl groups, $C_1$-$C_4$ alkoxy groups, and halogen atoms. $R^1$ is preferably a phenyl group, 4-methylphenyl group, 4-methoxyphenyl group, or 4-chlorophenyl group, more preferably a phenyl group.

In Compound (3), $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group. $R^3$ is preferably a hydrogen atom, benzyl group, methoxymethyl group, benzoyl group, or triethylsilyl group, more preferably a hydrogen atom.

In Compound (3), $R^4$ represents a formyl group, acetyl group, benzoyl group, tert-butoxycarbonyl group, or benzyloxycarbonyl group. $R^4$ is preferably a benzoyl group or a tert-butoxycarbonyl group.

In Compound (3), $R^5$ represents a $C_1$-$C_4$ alkyl. $R^5$ is preferably a methyl group, ethyl group, 1-propyl group, 2-propyl group, 1-butyl group, 2-butyl group, isobutyl group, or tert-butyl group, preferably a methyl group or ethyl group.

Examples of the acid chloride to be used in the esterification reaction include thionyl chloride, oxalyl chloride, and acetyl chloride. The acid chloride is preferably thionyl chloride.

The temperature during the esterification reaction is preferably 0 to 30° C., more preferably 0 to 20° C. The aging time after the addition of the acid chloride is preferably 30 minutes to 6 hours, more preferably 1 to 3 hours.

After aging, the 3-phenylisoserine derivative is isolated at 0 to 30° C. The 3-phenylisoserine derivative is preferably precipitated as crystals by crystallization. By taking advantage of low solubility of the desired product in the $C_1$-$C_4$ aliphatic alcohol, the desired product can be obtained at high purity by separation from the mother liquor by a solid-liquid separation operation such as filtration or centrifugation followed by a drying step. When a concentration isolation operation is carried out at a temperature of about 50° C. for the purpose of increasing the crystallization yield of the desired product, the desired product cannot be obtained at high purity because of a decrease in the purity.

EXAMPLES

Our method is described below by way of Examples.

In the Examples, the chemical purity was measured by the following method.

Chemical Purity Analysis Method

Sample Preparation

About 20 mg of each sample was accurately weighed, and placed in a 25-mL measuring flask. The sample was then diluted by adding 50% aqueous acetonitrile solution to the marked line.

Analysis conditions for high-performance liquid chromatography (HPLC)

Column: Mightsil RP-18 GP 4.6-mm diameter×250 mm, 5 μm (Kanto Chemical Co., Inc.)

Mobile phase: A: 20 mM aqueous sodium dihydrogen phosphate solution (whose pH was adjusted to 2.1 with phosphoric acid)

B: acetonitrile

Program composition: $A/B$=90/10 (Minute 0 to 10)→$A/B$=30/70 (Minute 25)→$A/B$=30/70 (Minute 25 to 35)→$A/B$=90/10 (Minute 40)→$A/B$=90/10 (Minute 40 to 45)

Flow rate: 1.0 mL/minute

Column temperature: 40° C.

Measurement wavelength: 254 nm

Sample volume: 10 μL

Retention time: 20.2 minutes (N-benzoyl-3-phenylisoserine)
22.2 minutes (N-benzoyl-3-phenylisoserine methyl ester)
22.1 minutes (N-tert-butoxycarbonyl-3-phenylisoserine)
24.6 minutes (N-tert-butoxycarbonyl-3-phenylisoserine methyl ester)

Example 1

In a 2-L four-necked flask equipped with a thermometer, condenser, and stirrer, 120 g (0.551 mol) of (2R,3S)-3-phenylisoserine hydrochloride was placed, and 720 g of water and 91.9 g (1.103 mol) of 48% aqueous sodium hydroxide solution were further added thereto. At about 20° C., 79.1 g (0.562 mol) of benzoyl chloride was added dropwise to the resulting mixture while the pH in the system was kept at 9 to 12 by addition of 46.9 g (0.562 mol) of 48% aqueous sodium hydroxide solution. The resulting mixture was subjected to aging at almost the same temperature for 1 hour. Subsequently, 360 g of tetrahydrofuran and 120 g of toluene were added to the mixture, and then 58.6 g (0.562 mol) of 35% aqueous hydrochloric acid solution was added dropwise thereto at about 20° C. The pH of the reaction liquid after the dropwise addition was 2.2. To the organic layer separated after leaving the reaction liquid to stand, 120 g of water, 120 g of tetrahydrofuran, and 120 g of toluene were added, and then extraction washing was carried out. After leaving the resulting liquid to stand, the separated organic layer was placed in a 2-L four-necked flask equipped with a thermometer, condenser, stirrer, and Dean-Stark apparatus, and then concentrated under reduced pressure while removing the contained water. To the resulting concentrate, 840 g of methanol was added, and concentration under reduced pressure was continued until the liquid in the can reduced to 650 g. The internal liquid after the concentration contained 1.1% water and 9.7% tetrahydrofuran. Subsequently, 68.9 g (0.579 mol) of thionyl chloride was added dropwise thereto at about 20° C., and the resulting mixture was cooled to about 5° C., followed by filtering of the precipitated crystals, washing of the crystals with 80 g of methanol, and then drying of the crystals under vacuum to obtain 141.3 g of (2R,3S)—N-benzoyl-3-phenylisoserine methyl ester as white crystals (chemical purity: 99.3%, yield: 85.6%).
$^{1}$H-NMR (CDCl$_3$, 400 MHz) δ ppm: 7.78-7.76 (m, 2H), 7.53-7.29 (m, 8H), 6.98 (d, 1H), 5.75 (d, 1H), 4.64 (d, 1H), 3.84 (s, 3H), 3.29 (d, 1H)
m.p.: 183-185° C.

Example 2

In a 300-mL four-necked flask equipped with a thermometer, condenser, and stirrer, 10 g (0.046 mol) of (2R,3S)-3-phenylisoserine hydrochloride was placed, and 50 g of water, 40 g of tetrahydrofuran, and 7.7 g (0.092 mol) of 48% aqueous sodium hydroxide solution were further added thereto. At about 20° C., 11.0 g (0.051 mol) of di-tert-butyl dicarbonate was added dropwise to the mixture, and the mixture was then subjected to aging at about 40° C. for 4 hours. Subsequently, 10 g of toluene was added to the mixture, and then 7.2 g (0.069 mol) of 35% aqueous hydrochloric acid solution was added dropwise thereto at about 20° C. The pH of the reaction liquid after the dropwise addition was 5.0. After leaving the resulting liquid to stand, the separated organic layer was placed in a 200-mL four-necked flask equipped with a thermometer, condenser, stirrer, and Dean-Stark apparatus, and then concentrated under reduced pressure while removing the contained water. To the resulting concentrate, 50 g of methanol was added, and concentration under reduced pressure was continued until the liquid in the can reduced to 35 g. The internal liquid after the concentration contained 1.0% water and 8.6% tetrahydrofuran. Subsequently, 5.7 g (0.048 mol) of thionyl chloride was added dropwise thereto at about 10° C., and the resulting mixture was cooled to about 5° C., followed by filtering of the precipitated crystals, washing of the crystals with 10 g of methanol, and then drying of the crystals under vacuum to obtain 8.1 g of (2R,3S)—N-tert-butoxycarbonyl-3-phenylisoserine methyl ester as white crystals (chemical purity: 99.0%, yield: 60.0%).
$^{1}$H-NMR (CDCl$_3$, 400 MHz) δ ppm: 7.37-7.29 (m, 5H), 5.40 (d, 1H), 5.22 (d, 1H), 4.49-4.48 (m, 1H), 3.84 (s, 3H), 1.62 (s, 1H), 1.43 (s, 1H)
m.p.: 131-133° C.

Example 3

The same operation as in Example 1 was carried out except that 1,2-dimethoxyethane was used instead of tetrahydrofuran as the extraction solvent in the extraction step of Example 1. As a result, 137.5 g of (2R,3S)—N-benzoyl-3-phenylisoserine methyl ester was obtained as white crystals (chemical purity: 99.5%, yield: 83.3%).

Comparative Example 1

The same operation as in Example 1 was carried out except that toluene was used instead of tetrahydrofuran as the extraction solvent in the extraction step of Example 1. As a result, (2R,3S)—N-benzoyl-3-phenylisoserine as an intermediate could be hardly extracted into the organic layer. To evaluate the performance of the extraction solvent, solubility of (2R,3S)—N-benzoyl-3-phenylisoserine was investigated for comparison. The results are shown in Table 1.

Comparative Example 2

The same operation as in Example 1 was carried out except that cyclopentyl methyl ether was used instead of tetrahydrofuran as the extraction solvent in the extraction step of Example 1. As a result, (2R,3S)—N-benzoyl-3-phenylisoserine as an intermediate could be hardly extracted into the organic layer. To evaluate the performance of the extraction solvent, solubility of (2R,3S)—N-benzoyl-3-phenylisoserine was investigated for comparison. The results are shown in Table 1.

Comparative Example 3

The same operation as in Example 1 was carried out except that methyl-tert-butyl ether was used instead of tetrahydrofuran as the extraction solvent in the extraction step of Example 1. As a result, (2R,3S)—N-benzoyl-3-phenylisoserine as an intermediate could be hardly extracted into the organic layer. To evaluate the performance of the extraction solvent, solubility of (2R,3S)—N-benzoyl-3-phenylisoserine was investigated for comparison. The results are shown in Table 1.

Comparative Example 4

The same operation as in Example 1 was carried out except that acetonitrile was used instead of tetrahydrofuran as the extraction solvent in the extraction step of Example 1.

As a result, (2R,3S)—N-benzoyl-3-phenylisoserine as an intermediate could be hardly extracted into the organic layer. To evaluate the performance of the extraction solvent, solubility of (2R,3S)—N-benzoyl-3-phenylisoserine was investigated for comparison. The results are shown in Table 1.

TABLE 1

|  | Protecting group | Solvent species | Solubility (20° C.) | Solubility (40° C.) |
|---|---|---|---|---|
| Example 1 | Benzoyl group | Tetrahydrofuran | 9.2 wt % | 11.6 wt % |
| Example 2 | tert-Butoxycarbonyl group | Tetrahydrofuran | 10.1 wt % | 12.2 wt % |
| Example 3 | Benzoyl group | 1,2-Dimethoxyethane | 12.7 wt % | 13.6 wt % |
| Comparative Example 1 | Benzoyl group | Toluene | <0.1 wt % | <0.1 wt % |
| Comparative Example 2 | Benzoyl group | Cyclopentyl methyl ether | 0.4 wt % | 0.4 wt % |
| Comparative Example 3 | Benzoyl group | Methyl-tert-butyl ether | 0.2 wt % | 0.4 wt % |
| Comparative Example 4 | Benzoyl group | Acetonitrile | 2.2 wt % | 2.9 wt % |

Table 1 shows comparison of the solubilities of N-protected-3-phenylisoserine in the extraction solvents. It can be seen that N-protected-3-phenylisoserine shows high solubilities in the solvents used in the Examples.

Comparative Example 5

The same operation as in Example 1 was carried out except that a concentration isolation operation was carried out after performing dropwise addition of thionyl chloride and increasing the temperature to about 50° C. As a result, 117.4 g of (2R,3S)—N-benzoyl-3-phenylisoserine methyl ester was obtained as white crystals (chemical purity: 77.7%, yield: 55.3%). However, impurities remained in an amount of as much as about 20%, and the yield largely decreased.

Comparative Example 6

As a comparative example, a method of obtaining N-benzoyl-3-phenylisoserine ester by esterification of crystals isolated by solid-liquid separation is described.

In a 300-L four-necked flask equipped with a thermometer, condenser, and stirrer, 10 g (0.046 mol) of (2R,3S)-3-phenylisoserine hydrochloride was placed, and 100 g of water and 7.7 g (0.092 mol) of 48% aqueous sodium hydroxide solution were further added thereto. At about 20° C., 6.6 g (0.047 mol) of benzoyl chloride was added dropwise to the resulting mixture while the pH in the system was kept at 9 to 12 by addition of 3.8 g (0.046 mol) of 48% aqueous sodium hydroxide solution. The resulting mixture was subjected to aging at almost the same temperature for 1 hour. Subsequently, 4.8 g (0.046 mol) of 35% aqueous hydrochloric acid solution was added dropwise thereto at about 20° C. The pH of the reaction liquid after the dropwise addition was 2.7. The content of the can after the dropwise addition was in a state of a whipped slurry of fine crystals. The slurry was transferred to a Kiriyama funnel, and suction filtration was carried out by reducing the pressure to perform solid-liquid separation. As a result, not less than two hours were required to obtain (2R,3S)—N-benzoyl-3-phenylisoserine as wet crystals. The wet crystals were dried under reduced pressure, and then quantified. As a result, 11.0 g of dry crystals were obtained (chemical purity: 94.2%, yield: 84.2%, loss on drying: 66.1%). Subsequently, 100 g of methanol was added to the crystals, and 4.6 g (0.039 mol) of thionyl chloride was added dropwise thereto at about 20° C.

The resulting mixture was cooled to about 5° C., and the precipitated crystals were collected by filtration, followed by washing with 10 g of methanol and drying under vacuum to obtain 6.8 g of (2R,3S)—N-benzoyl-3-phenylisoserine methyl ester as white crystals (chemical purity: 98.2%, process yield: 58.7%, total yield: 49.4%).

INDUSTRIAL APPLICABILITY

By our method of producing a 3-phenylisoserine derivative, a 3-phenylisoserine derivative having a purity of not less than 99% can be obtained. A 3-phenylisoserine derivative having a purity of not less than 99% is useful as a material for pharmaceuticals.

The invention claimed is:

1. A method of producing a 3-phenylisoserine derivative, comprising:

protecting an amino group of a compound represented by General Formula (1):

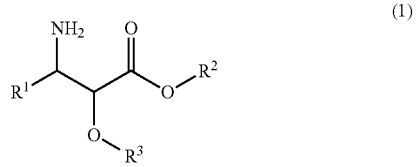

wherein $R^1$ represents a phenyl group, or a phenyl group having a substituent; $R^2$ represents an alkali metal, alkaline earth metal, or nitrogen base; and $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group in water or a mixed solvent containing water to obtain a compound represented by General Formula (2):

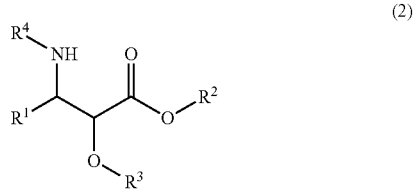

wherein $R^1$ represents a phenyl group, or a phenyl group having a substituent; $R^2$ represents an alkali metal, alkaline earth metal, or nitrogen base; $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group; and $R^4$ represents a formyl group, acetyl group, benzoyl group, tert-butoxycarbonyl group, or benzyloxycarbonyl group;

extracting the compound represented by General Formula (2) with a $C_4$ ether-based solvent;

replacing at least part of the $C_4$ ether-based solvent with a $C_1$-$C_4$ aliphatic alcohol while removing the $C_4$ ether-based solvent and water to perform an esterification reaction; and isolating a 3-phenylisoserine derivative represented by General Formula (3) at 0 to 30° C.:

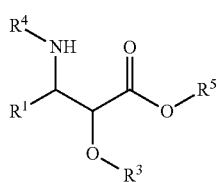

(3)

wherein $R^1$ represents a phenyl group, or a phenyl group having a substituent; $R^3$ represents a hydrogen atom, methyl group, benzyl group, p-methoxybenzyl group, tert-butyl group, methoxymethyl group, 2-tetrahydropyranyl group, ethoxyethyl group, acetyl group, pivaloyl group, benzoyl group, trimethylsilyl group, triethylsilyl group, or tert-butyldimethylsilyl group; $R^4$ represents a formyl group, acetyl group, benzoyl group, tert-butoxycarbonyl group, or benzyloxycarbonyl group; and $R^5$ represents a $C_1$-$C_4$ alkyl group.

2. The method according to claim 1, wherein the $C_4$ ether-based solvent is tetrahydrofuran or 1,2-dimethoxyethane.

3. The method according to claim 1, wherein the $C_1$-$C_4$ aliphatic alcohol is methanol or ethanol.

4. The method according to claim 1, wherein $R^4$ is a benzoyl group or tert-butoxycarbonyl group.

5. The method according to claim 2, wherein the $C_1$-$C_4$ aliphatic alcohol is methanol or ethanol.

6. The method according to claim 2, wherein $R^4$ is a benzoyl group or tert-butoxycarbonyl group.

7. The method according to claim 3, wherein $R^4$ is a benzoyl group or tert-butoxycarbonyl group.

* * * * *

UNITED STATES PATENT AND TRADEMARK OFFICE
CERTIFICATE OF CORRECTION

PATENT NO. : 10,087,139 B2
APPLICATION NO. : 15/554743
DATED : October 2, 2018
INVENTOR(S) : Hiraga et al.

Page 1 of 1

It is certified that error appears in the above-identified patent and that said Letters Patent is hereby corrected as shown below:

On the Title Page

At (71) Applicant, please change "CHhemicals" to -- Chemicals --.

Signed and Sealed this
Thirtieth Day of July, 2019

Andrei Iancu
*Director of the United States Patent and Trademark Office*